(12) United States Patent
Bahr et al.

(10) Patent No.: US 6,665,372 B2
(45) Date of Patent: Dec. 16, 2003

(54) X-RAY DIFFRACTOMETER

(75) Inventors: Detlef Bahr, Karlsruhe (DE); Norbert Kuhnmuench, Karlsruhe (DE)

(73) Assignee: Bruker Axs GmbH, Karlsruhe (DE)

( * ) Notice: Subject to any disclaimer, the term of this patent is extended or adjusted under 35 U.S.C. 154(b) by 0 days.

(21) Appl. No.: 10/202,905

(22) Filed: Jul. 26, 2002

(65) Prior Publication Data

US 2003/0043965 A1 Mar. 6, 2003

(30) Foreign Application Priority Data

Aug. 28, 2001 (DE) .......................... 101 41 958

(51) Int. Cl.$^7$ .............................................. G01N 23/20
(52) U.S. Cl. .......................................... 378/71; 378/84
(58) Field of Search ................................. 378/71, 84

(56) References Cited

U.S. PATENT DOCUMENTS 6,310,937 B1 * 10/2001 Van Den Hoogenhof ..... 378/71

FOREIGN PATENT DOCUMENTS

| DE | 198 20 861 | 11/1999 |
| EP | 0 183 043 | 10/1985 |
| WO | WO 97/05474 | 2/1997 |

OTHER PUBLICATIONS

"Diffraction Solutions D8 Advance", Bruker AXS Analytical X–Ray Systems GmbH, Karlsruhe, 1997.
"X' Pert–MRD", Philips Analytical X–Ray B.V., Almelo, The Netherlands.
"X–ray Diffraction Apparatus", Patent Abstracts of Japan, 0 432 4348, (1992).

* cited by examiner

Primary Examiner—Craig E. Church
(74) Attorney, Agent, or Firm—Paul Vincent

(57) ABSTRACT

An X-ray diffractometer comprising an X-ray source (10) from which X-rays are guided to a sample (11) to be investigated, an X-ray detector (12) for receiving X-rays diffracted or scattered from or reflected by the sample (11), and a goniometer for adjustment of sequential relative angular positions between the X-ray source (10), the sample (11) and the X-ray detector (12) for detecting X-ray diffraction lines, X-ray scattered signals or X-ray reflectograms of the sample (11) to be investigated, wherein the X-rays can be guided at least sectionally along different optical paths, is characterized in that the X-rays can be guided from a position 1 to a position 2 along n≧2 different switchable optical paths, wherein the different optical paths are rigidly disposed relative to each other between position 1 and position 2 and form a unit (13), wherein the sample (11) assumes either position 1 or position 2 and wherein the switching over between the different optical paths can be effected by turning the unit (13) relative to the sample (11) about the sample position. Due to its considerably more compact structure compared to conventional arrangements, the inventive arrangement requires considerably less space while maintaining full relative motion of the parts, wherein the arrangement permits omission of expensive components, in particular detectors and associated measurement electronics.

13 Claims, 2 Drawing Sheets

X-RAY DIFFRACTOMETER

This application claims Paris Convention priority of DE 101 41 958.9 filed Aug. 28, 2001 the complete disclosure of which is hereby incorporated by reference.

BACKGROUND OF THE INVENTION

The invention concerns an X-ray diffractometer with an X-ray source from which X-rays are guided to a sample to be investigated, comprising an X-ray detector for receiving X-rays diffracted or scattered from or reflected by the sample, and a goniometer for adjustment of sequential relative angular positions between the X-ray source, the sample and the X-ray detector for detecting X-ray diffraction lines, X-ray scattered signals or X-ray reflectograms of the sample to be investigated, wherein the X-rays can be guided, at least in sections, along different optical paths.

An X-ray diffractometer arrangement of this type is known e.g. from the company leaflet "X'Pert-MRD" (Philips Analytical X-Ray B.V., Almelo, The Netherlands).

The company leaflet "DIFFRACTION SOLUTIONS D8 ADVANCE" (Bruker AXS Analytical X-ray Systems GmbH, 1997) describes in detail the functional principles of an X-ray diffractometer. Diffractometers of this type can handle a broad variety of analytical tasks in the most differing of fields, such as polymer chemistry, glass production, coating technology, ceramic production, pharmaceuticals, mineralogy, geology, semiconductor and superconductor technology, power plant technology, as well as in archaeology, environment analysis and criminology. Such an X-ray diffractometer facilitates high accuracy routine applications and also demanding special applications in powder diffractometry, such as qualitative and quantitative phase analysis, determination of crystal size and crystallographic investigations. In contrast to a multi-channel spectrometer, an X-ray diffractometer of this type comprises a goniometer for setting sequential relative angular positions between the source, the sample and the detector for carrying out e.g. "Step Scans" or continuous scans. All components mounted on the goniometer can be replaced in a rapid, simple and reproducible fashion.

The above-cited Phillips company leaflet "X-Pert-MRD" describes an X-ray diffractometer with which the X-rays can be guided along different optical paths. The system, however, requires a considerably larger number of components, i.e. several detectors and associated measurement electronics. Moreover, the complex arrangement requires a large amount of space due to its geometric structure which limits the respective angular region which can be analytically detected.

In contrast thereto, it is the object of the invention to present a diffractometer arrangement with the above-mentioned features having as simple a topological construction as possible and of considerably more compact structure to require considerably less space while maintaining full relative motion of the parts, and with reduced amounts of expensive components, in particular detectors and associated measuring electronics or optionally additional X-ray tubes with associated high voltage and cooling water supplies.

SUMMARY OF THE INVENTION

This object is achieved in accordance with the invention in a surprisingly simple and also effective fashion in that the X-rays emitted at a selected detection angle are guided from a position 1 to a position 2 along $n \geq 2$ different, switchable optical paths, wherein the different optical paths are rigidly adjusted relative to one another between position 1 and position 2 to form a unit, wherein the sample assumes either position 1 or position 2, and wherein switching between the different optical paths can be effected by turning the unit relative to the sample, about the sample position to align a selected optical oath at the detection angle and by blocking all non-selected optical paths.

In this manner, construction of an X-ray diffractometer of this type is facilitated using means which are technically easy to realize. The useful angular region is considerably extended compared to the known arrangement for all possible applications using the different optical paths. In this connection, the optical paths can be constructed such that only one single X-ray source on the primary side of the sample and only one single detector on the secondary side of the sample are required.

In a particularly advantageous embodiment of the inventive X-ray diffractometer, the sample is disposed at position 1 and the detector at position 2. The X-ray radiation from the sample can thereby be accommodated along different optical paths with different physical properties using one single detector and one single detector electronics thereby avoiding additional, expensive components.

In an alternative embodiment of the invention, the source is disposed at position 1 and the sample at position 2. In this embodiment, the sample can be illuminated with differently prepared or selected X-rays to facilitate different types of measurement without requiring reconfiguration, realignment, and adjustment between measurements.

One embodiment of the inventive arrangement is particularly preferred with which at least one of the optical paths contains a dispersive or reflecting X-ray optical element such as e.g. a crystal, a channelcut crystal, a mosaic crystal, a multi-layered structure, an X-ray mirror, a diffraction grid or another dispersive or reflecting X-ray optical element. These elements produce substantially monochromatic X-ray radiation from an impinging polychromatic X-ray and can be applied to both the X-ray radiation incident on the sample as well as to the X-rays emanating from the sample.

One embodiment of the inventive X-ray diffractometer is particularly preferred with which at least one of the optical paths contains neither a dispersive nor a reflecting X-ray optical element. Such an optical path permits direct passage of X-rays between positions 1 and 2, to provide a particularly high radiation intensity through direct optical guidance.

In an advantageous further development of this embodiment, the direct optical path has an X-ray lens which can be designed either as a converging lens, a diverging lens or a parallelizing half lens.

One embodiment of the invention is particularly advantageous wherein at least one of the optical paths contains an adjustable and/or exchangeable collimator. This allows adjustment of nearly any intensity for the X-rays passing through the respective optical path and the collimating out of undesired scattered light.

One embodiment is also advantageous wherein at least one of the optical paths includes a shutter. This also eliminates disturbing light. Moreover, certain specific optical paths can thereby be blanked out of the measurement.

One embodiment of the inventive X-ray diffractometer is particularly simple, having only n=2 different, switchable optical paths.

For somewhat more complex embodiments n>2 different switchable optical paths are provided. In simple versions, these may be coplanar to substantially concentrate the optical paths in a single plane.

For more complex versions, not all optical paths are in one common plane but are deflected within certain solid angular regions. These variants are mostly useful for point focus applications.

In a particularly advantageous further development of these embodiments of the inventive X-ray diffractometer, there are several optical paths which are bent relative to that optical path directly connecting position 1 to position 2, each bent optical path being composed of two straight partial paths, wherein a dispersive or reflecting X-ray optical element is disposed at the bending point and the bending points of at least some of these partial paths are disposed on a common circle about the direct optical path between position 1 and position 2.

A main application of this latter development is for cases in which a common wavelength is selected using one single crystal material and a common grating. The resolution, the divergence, the intensity and monochromaticity can thereby be differently adjusted along the different optical paths, depending on the particular requirements and without having to use different crystal materials.

For special embodiments of the invention, the units having the different optical paths, rigidly adjusted relative to one another, can be provided on both source and also detector sides. These embodiments are characterized in that the source is disposed at the position 1 and the sample at the position 2 which, for its part, now corresponds to a position 1' with the detector being disposed at an associated position 2'. In this fashion, the advantages of the invention can be utilized on "both sides of the sample".

In contrast to the inventive X-ray diffractometers, multichannel X-ray spectrometers do not have goniometers with movable optical paths. WO 97/05474 A1 describes e.g. a multi-channel X-ray spectrometer with optical paths which are switchable through rotation of a crystal drum. However, the individual optical path as such cannot be moved but is always rigidly disposed at the same location within the apparatus.

DE 198 20 861 A1 describes a multi-channel X-ray spectrometer with two optical paths which require only one detector and one single measuring electronics. It does not provide for motion of the optical paths which are rigidly disposed in the apparatus. In particular no goniometer is thereby provided.

Further advantages can be extracted from the drawing and the description. The features mentioned above and below can be used in accordance with the invention either individually or collectively in any arbitrary combination. The embodiments shown and described cannot be regarded as exhaustive enumeration but rather have exemplary character for describing the invention.

The invention is shown in the drawing and is explained in more detail by means of embodiments:

DESCRIPTION OF THE PREFERRED EMBODIMENT

Figure 1:
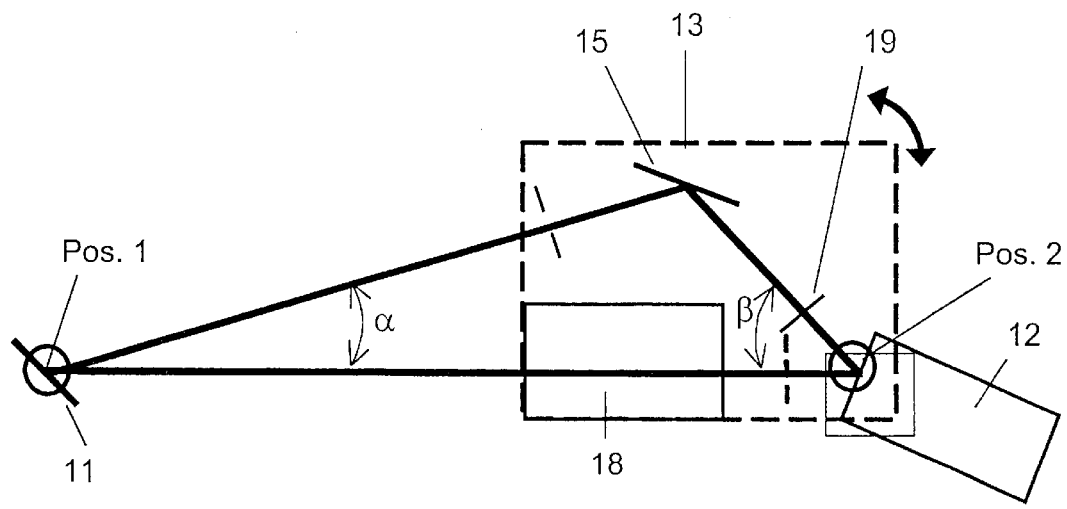
FIG. 1 shows a schematic representation of a unit, having two different optical paths which can be pivoted relative to the sample position, and a detector as part of the inventive X-ray diffractometer.

The detecting part of an inventive X-ray diffractometer schematically shown in FIG. 1 comprises a sample 11 at position 1, a detector 12 at position 2 and two optical paths which are rigidly adjusted relative to each other, one of which extends in a straight line from the position 1 where the sample 11 is disposed through a diaphragm system 18 (shown as a box with adjustable and/or exchangeable diaphragms) to the position 2 at the entry of the X-ray detector 12. The other optical path initially extends at an angle α from the sample position along a first straight section to a dispersive or reflecting X-ray optical element 15 and, in a second straight section disposed at an angle β relative to the first optical path, from this location to the position 2 at the entry of the X-ray detector 12. The diffracted optical path can be blanked with respect to the detector 12 or vice versa using a shutter 19.

Both optical paths and the detector 12, the X-ray optical element 15 and the diaphragm system 18 are rigidly adjusted relative to each other and can be commonly pivoted as a unit 13 about the position 1 relative to the sample 11, wherein either the unit 13 or the sample 11 is thereby moved.

Figure 2:
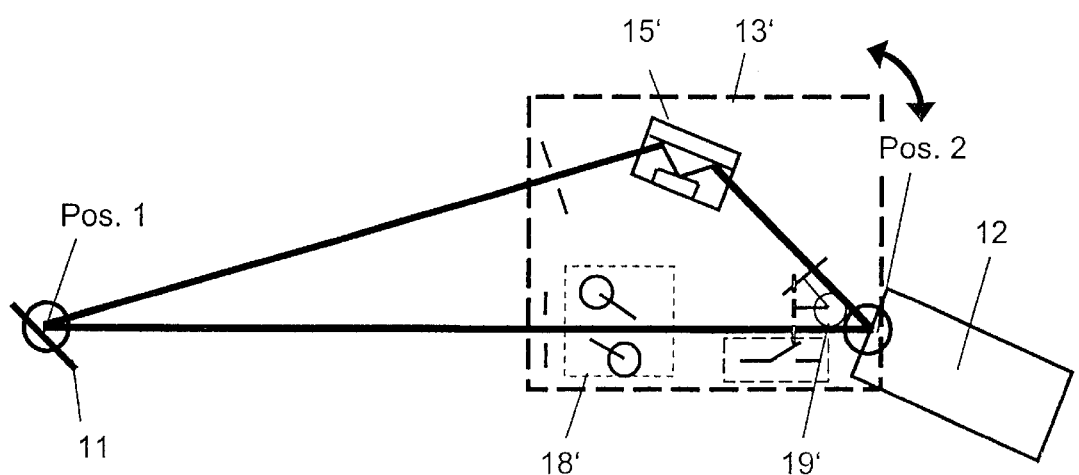
FIG. 2 like FIG. 1, wherein the pivotable unit is provided with other X-ray optical elements.

The unit 13' schematically shown in FIG. 2 can also be pivoted relative to position 1 of the sample 11 and also contains a dispersive X-ray optical element 15' in the form of a Channelcut crystal in addition to the two different optical paths which are rigidly disposed relative to each other and which extend from position 1 of sample 11 to position 2 at the entry of the detector 12. The diffracted optical path can be blanked with respect to the detector 12 by means of a shutter 19' whose electric actuator is also schematically indicated. The electric actuator can be e.g. in the form of a microswitch. The unit 13' also comprises a variable diaphragm unit 18' along the straight optical path with which the X-ray light along the straight optical path can be gradually collimated.

Figure 3:
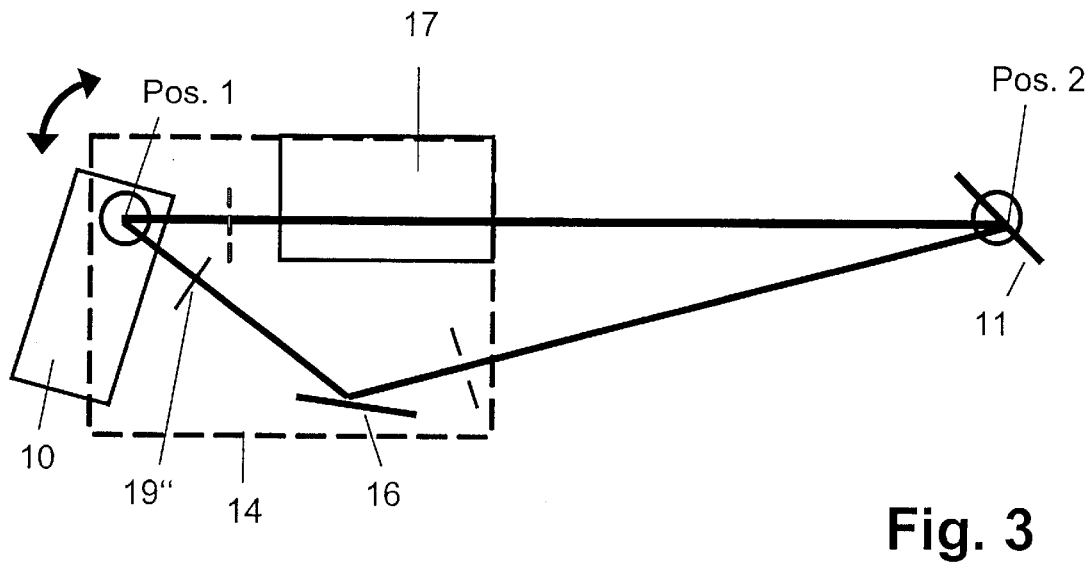
FIG. 3 a unit with two optical paths and an X-ray source which can be pivoted together with the unit, relative to the sample.

FIG. 3 schematically shows the source side of an inventive X-ray diffractometer. An X-ray source 10 is disposed with its source, usually its electron focus, at the position 1 and the sample 11 is located at position 2. A unit 14 is also provided which can be pivoted relative to the sample location. Two different optical paths, i.e. a straight and a diffracted optical path, can be rigidly adjusted relative to each other and pivoted with respect to the sample, located at position 2. The unit 14 comprises an X-ray optical element 16 which can e.g. contain a means for monochromatization of the X-ray light travelling along the diffracted optical path.

In this embodiment, an X-ray lens (schematically shown as a box) is disposed in the straight optical path and can focus X-ray light emanating from the X-ray source 10, within a certain diverging angle, onto the sample 11. A shutter 19" is provided after the exit from the X-ray source 10 to collimate out the diffracted or straight optical path with respect to the sample 11.

Figure 4:
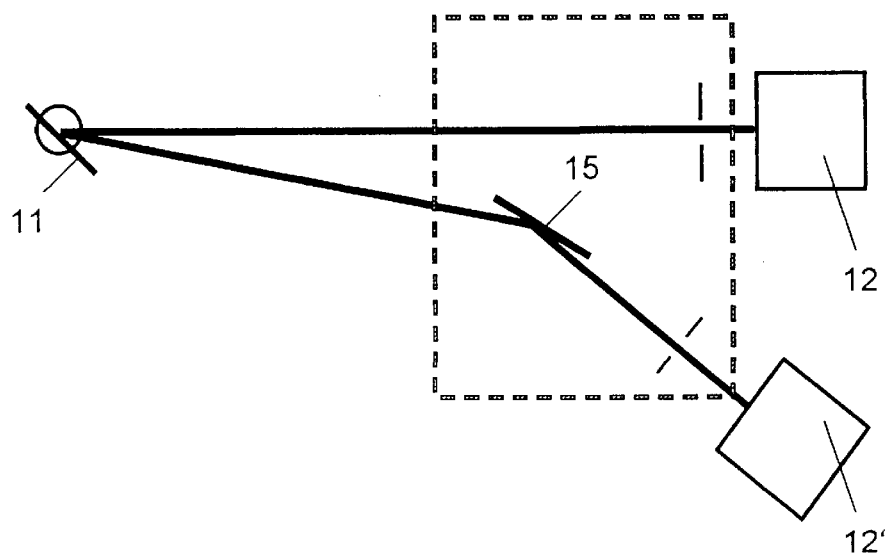
FIG. 4 part of a diffractometer according to prior art with two optical paths having a detector disposed at each end.

By means of comparison, FIG. 4 shows the detecting side of an X-ray diffractometer according to prior art, wherein two rigidly adjusted optical paths are provided starting from the sample 11, one of which extends directly to a detector 12 and the other to a further detector 12' via an X-ray optical element 15. When the two optical paths are pivoted about the location of the sample 11, each of the two detectors limits the possibly geometrical range of the other.

In other embodiments of the invention (not shown in the drawing), one or more pivotable units having optical paths which are fixed relative to each other can be provided on the side of the source or on the side of the detector. In this case, the source 10 is disposed at the position 1, the sample 11 at the position 2, which corresponds to a position 1' and the detector 12 is disposed at a position 2', wherein the positions 1' and 2' are associated with another for assuming the function of the above-discussed positions 1 and 2 to thereby realize the invention on both sides of the sample 11, about which the corresponding units can rotate.

Further embodiments (not shown in greater detail in the drawing) can also contain units with more than two different optical paths. These can extend away from the position 1 and towards the position 2, either in a plane or within a solid angle range.

We claim:

1. An X-ray diffractometer for investigation of a sample, the diffractometer having at least one section in which X-rays can be guided along different optical paths, the diffractometer comprising:

an X-ray source;

a sample location onto which X-rays from said source are directed; an X-ray detector for receiving X-rays which are at least one of diffracted from, scattered from, and reflected by the sample at a selected detection angle;

a goniometer cooperating with said source, said sample location and said detector for changing said detection angle to adjust sequential relative angular positions between said source, the sample and said detector to detecting at least one of X-ray diffraction lines, X-ray scattered signals, and X-ray reflectograms of the sample;

an optical unit having $n \geq 2$ different, switchable optical paths for guiding X-rays from a first position to a second position downstream of said first position along a selected optical path, wherein said $n \geq 2$ different optical paths have fixed, unchanging positions relative to each other between said first and said second positions, wherein said sample location is disposed at one of said first position and said second positions;

means for turning said optical unit relative to the sample and about said sample location to cause X-rays at said detection angle to travel along a different one of said $n \geq 2$ optical paths; and means for preventing X-rays emanating from the sample at angles other than said detection angle from reaching said detector along a non-selected one of said $n \geq 2$ different optical paths.

2. The X-ray diffractometer of claim 1, wherein the sample is disposed at said first position and said detector at said second position.

3. The X-ray diffractometer of claim 1, wherein said source is disposed at said first position and said sample at said second position.

4. The X-ray diffractometer of claim 1, wherein at least one of said $n \geq 2$ optical paths comprises at least one of a dispersive optical element, a reflecting X-ray optical element, a crystal, a channelcut crystal, a mosaic crystal, a multi-layer structure, an X-ray mirror, and a diffraction grid.

5. The X-ray diffractometer of claim 1, wherein at least one of said $n \geq 2$ optical paths contains neither a dispersive nor a reflecting X-ray optical element.

6. The X-ray diffractometer of claim 5, wherein at least one of said $n \geq 2$ optical paths contains an X-ray lens.

7. The X-ray diffractometer of claim 1, wherein at least one of said $n \geq 2$ optical paths contains at least one of an adjustable and a replaceable diaphragm.

8. The X-ray diffractometer of claim 1, wherein at least one of said $n \geq 2$ optical paths has a shutter.

9. The X-ray diffractometer of claim 1, wherein $n=2$.

10. The X-ray diffractometer of claim 1, wherein $n>2$, said $n>2$ optical paths extending in a coplanar fashion.

11. The X-ray diffractometer of claim 1, wherein $n>2$, with not all of said $n>2$ optical paths being disposed in a common plane.

12. The X-ray diffractometer of claim 11, wherein one of said $n>2$ optical paths is a straight optical path connecting said first and said second positions in a substantially straight-line manner and a plurality of said $n>2$ optical paths each comprise two partial paths meeting at a bending point to define a bent, two-legged path extending between said first and said second positions, wherein at least one of a dispersive and a reflecting X-ray optical element is disposed at said bending point, said bending points of at least some of said partial paths being disposed on a common circle about said straight optical path.

13. The X-ray diffractometer of claim 1, further comprising a second optical unit having $n \geq 2$ different, switchable optical paths for guiding X-rays from said second position to a third position downstream of said second position, wherein said source is disposed at said first position, said sample is disposed at said second position and said detector is disposed at said third position.

* * * * *